United States Patent
Krittian et al.

(10) Patent No.: US 9,986,966 B2
(45) Date of Patent: Jun. 5, 2018

(54) COMPUTATION METHOD OF RELATIVE CARDIOVASCULAR PRESSURE

(71) Applicant: OXFORD UNIVERSITY INNOVATION LTD., Oxford (GB)

(72) Inventors: Sebastian Benedikt Sylvester Krittian, Oxford (GB); Nicolas Smith, Oxford (GB)

(73) Assignee: OXFORD UNIVERSITY INNOVATION LIMITED, Oxford (GB)

(*) Notice: Subject to any disclaimer, the term of this patent is extended or adjusted under 35 U.S.C. 154(b) by 990 days.

(21) Appl. No.: 14/095,810

(22) Filed: Dec. 3, 2013

(65) Prior Publication Data
US 2014/0222354 A1 Aug. 7, 2014

Related U.S. Application Data

(60) Provisional application No. 61/733,130, filed on Dec. 4, 2012.

(51) Int. Cl.
*A61B 8/06* (2006.01)
*A61B 5/055* (2006.01)
(Continued)

(52) U.S. Cl.
CPC .............. *A61B 8/06* (2013.01); *A61B 5/0044* (2013.01); *A61B 5/021* (2013.01); *A61B 5/055* (2013.01);
(Continued)

(58) Field of Classification Search
None
See application file for complete search history.

(56) References Cited

U.S. PATENT DOCUMENTS

| | | | |
|---|---|---|---|
| 8,487,613 B2* | 7/2013 | McNeal | G01R 33/56316 324/306 |
| 8,675,940 B2* | 3/2014 | Gulsun | G06T 7/251 382/131 |

(Continued)

OTHER PUBLICATIONS

Ebbers, Tino; Farneback, Gunnar; Improving computation of cardiovascular relative pressure fields from velocity MRI; Jun. 25, 2009; JMRI vol. 30, Issue 1; p. 54-61.*

Escobar-Vargas, J.A.; Diamessis, P.J.; Van Loan, C.F.; The numerical solution of the pressure Poisson equation for the incompressible Navier-Stokes equations using a quadrilateral spectral multidomain penalty method; Dec. 5, 2011; Journal of Computational Physics.*

(Continued)

*Primary Examiner* — Gregory J Toatley
*Assistant Examiner* — Terence Stifter, Jr.
(74) *Attorney, Agent, or Firm* — Thomas | Horstemeyer, LLP

(57) ABSTRACT

The present invention provides a method for the determination of relative pressure fields from flow-sensitive data, the method comprising: applying a finite element discretization to the Pressure Poisson Equation (PPE):

$$b = f + \mu \Delta u - \rho \left( \frac{\partial u}{\partial t} + ((u - w) \cdot \nabla) u \right)$$

where vecter b is a function of a given blood velocity data, u represents the velocity, w the reference velocity, t the time, f a volume force, p the pressure and $\rho$ and $\mu$ the fluid density and viscosity, respectively, and wherein the PPE is now defined as the divergence of the above equation and gives a higher order derivative of the pressure field p: $\Delta p = \nabla \cdot b$.

24 Claims, 6 Drawing Sheets

(51) Int. Cl.
  *A61B 5/00* (2006.01)
  *G06F 17/50* (2006.01)
  *A61B 5/021* (2006.01)

(52) U.S. Cl.
  CPC ........ *A61B 5/7271* (2013.01); *G06F 17/5018* (2013.01); *G06T 2207/10076* (2013.01); *G06T 2207/30048* (2013.01); *G06T 2207/30104* (2013.01)

(56) References Cited

U.S. PATENT DOCUMENTS

2010/0130878 A1* 5/2010 Lasso ............... G06T 7/0012
  600/500
2012/0041318 A1* 2/2012 Taylor ............... A61B 5/02007
  600/504

OTHER PUBLICATIONS

Tyszka, J. Miichael; Laidlaw, David H.; Asa, Joesph W.; Silverman, Jeffrey M.; Three-dimensional, time-resolved (4D) relative pressure mapping using magnetic resonance imaging; Jul. 31, 2000; JMRI vol. 12, Issue 2; p. 321-329.*

Duarte, Fabian; Gormaz, Raul; Natesan, Srinivasan; Arbitrary Lagrangian-Eulerian method for Navier-Stokes equations with moving boundaries; May 8, 2004; Comput. Methods Appl. Mech. Engrg. 193; p. 4819-4836.*

Ebbers, Tino; Wigstrom, Lars; Bolger, Ann F.; Engvall, Jan; Karlsson, Matts; Estimation of Relative Cardiovascular Pressures Using Time-Resolved Three-Dimensional Phase Contrast MRI; 2001; Magnetic Resonance in Medicine 45:872-879.*

Lewis, R.W.; Ravindran, K.; Usmani, A.S.' Finite Element Solution of Incompressible Flows Using an Explicit Segregated Approach; 1995; Archives of Computational Methods in Engineering; vol. 2, 4, pp. 69-93.*

* cited by examiner

COMPUTATION METHOD OF RELATIVE CARDIOVASCULAR PRESSURE

TECHNICAL FIELD

The present invention generally relates to the computation of pressure of blood flow within soft tissue using medical imaging and more particularly, relates to a method for computing the relative pressure from flow sensitive data. In particular the present method is used for the computation of the relative cardiovascular pressure of subject-specific blood flow in relation to adjacent soft tissue movements. The present invention is particularly suitable, but not limited, for use where a patient has suffered a heart attack or other such pathological condition which affects the blood flow within the soft tissues. The present method can thus be used to non-invasively identify the amount of pressure produced by cardiovascular flows, from MRI data, due to temporal acceleration, spatial acceleration and viscous dissipation. The imaging data may also be from an ultrasound scanner or other such scanner. The present invention also has applications in the fields of Particle Imaging Velocimetry, which is an optical method of flow visualization, amongst others, such as determining the cabin pressure inside an airoplane.

BACKGROUND

In recent years, cardiac dysfunction has become the most common cause of death in the western world. Advances in imaging science and, more recently, computational physiology provide significant potential to circumvent many of the current limitations in diagnosis and therapy planning. A key element to the application of these technologies is the extraction of clinically relevant information from patient data.

To date, fluid mechanics models have been widely used to analyse cardiovascular blood flow and more recently been integrated with tissue mechanics to understand coupled cardiac function. The fluid domain behaviour has been evaluated based on numerical discretisation techniques. The flow domain has also been coupled numerically to solid mechanics models based on monolithic or even mixed approaches. In these models, both the intra-ventricular pressure and velocity fields are a direct consequence of the continuum mechanics principles of mass and momentum conservation as well as the imposed boundary conditions. These boundary conditions are the pressures on the inside surfaces of the heart chamber and vessel walls. The problem therefore, with these methods, is that boundary conditions must be imposed which leads to inaccurate calculation of the flow fields.

An alternative to calculating flow fields from pressure boundary conditions is to determine pressure from known flow fields. In this case the so-called Pressure Poisson Equation (PPE) can be derived directly from the well-known Navier-Stokes equations. This pressure information is in turn very valuable for the formulation of more realistic boundary conditions for the models described above. For example, the PPE has been used to determine relative pressure fields from a sequence of ultrafast cardiac Comupted Tomography (CT) images.

Ongoing clinical research has established phase contrast magnetic resonance velocity mapping as a useful tool to gain non-invasive insight into dynamic cardiovascular blood flow in a wide range of contexts. Of course, other imaging tools may also be used, such as ultrasound.

A similar approach as that used for the analysis of CT images, as described above, has been applied for the computation of flow pressure fields from MR velocity mapping. Their applied mathematical formulation is based on the assumption that the contribution of viscous terms to the pressure calculation can be neglected which holds true only for high Reynolds number flow. Furthermore, the underlying numerical discretisation requires an iterative solution in order to determine unknown boundary conditions. The need for applying these boundary conditions on the fluid domain further complicates the direct use of the actual imaging space as computational domain. As an alternative, multi-directional intra-cardiac flow relative to selected planes has been analysed, as well as the flow relative to volumes of acquisition. However, again these methods require an iterative solution to determine unknown boundary conditions.

It is, therefore, an object of the present invention to provide a method of computation of intra-vascular differences of pressure, directly from the velocity data.

SUMMARY

The present invention provides a method for the determination of relative pressure fields from flow-sensitive data, the method comprising: applying a finite element discretisation to the Pressure Poisson Equation (PPE):

$$b = f + \mu \Delta u - \rho \left( \frac{\partial u}{\partial t} + ((u - w) \cdot \nabla) u \right)$$

where vecter b is a function of a given blood velocity data, u represents the velocity, w the reference velocity, t the time, f a volume force, p the pressure and $\rho$ and $\mu$ the fluid density and viscosity, respectively, and wherein the PPE is now defined as the divergence of the above equation and gives a higher order derivative of the pressure field p:

$$\Delta p = \nabla \cdot b.$$

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
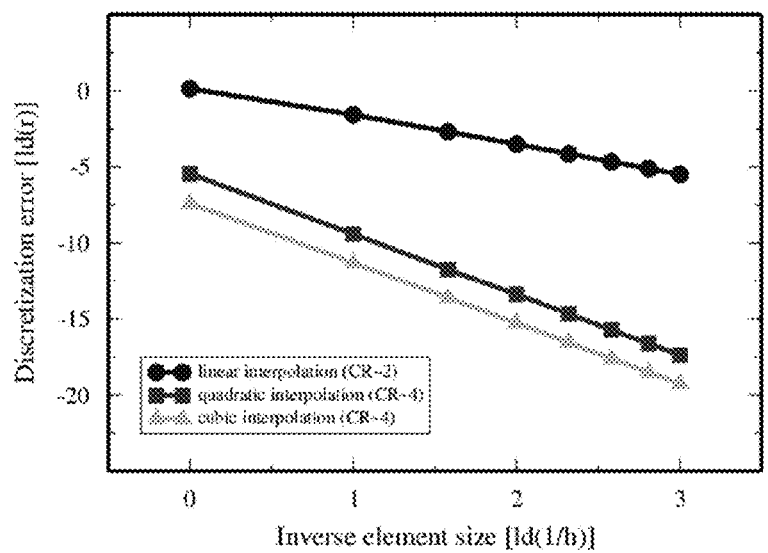
FIG. 1 is a graph illustrating the assessment of the convergence rate for the Poisson problem given in Equation (12) as given by the slope for various orders of interpolation.

Having summarized various aspects of the present disclosure, reference will now be made in detail to the description of the disclosure as illustrated in the drawings. While the disclosure will be described in connection with these drawings, there is no intent to limit it to the embodiment or embodiments disclosed herein. On the contrary, the intent is to cover all alternatives, modifications and equivalents included within the spirit and scope of the disclosure as defined by the appended claims.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

In order to fully enable the skilled person to understand the present invention, the mathematical background is firstly discussed.

Governing Equations

The pressure estimation process is based on the continuum mechanics principles of mass and momentum conservation. The underlying equations can be used to derive the PPE foundations needed for the pressure estimation process presented.

Computing the pressure distribution p that corresponds to a given incompressible flow field u, u is expected to satisfy the divergence-free condition $\nabla \cdot u \stackrel{!}{=} 0$. Following Newton's second law, the relative pressure distribution can be seen as a consequence of transient and convective momentum, viscous resistance and volume forces. Using the approach described below the separation of Pressure into these forces (transient and convective momentum, viscous resistance and volume forces) can be performed with the relative magnitudes and spatial-temporal patterns providing disease biomarkers. On an Arbitrary Lagrangian Eulerian (ALE) reference frame, this condition is formulated by the Navier-Stokes equations:

$$\rho\left(\frac{\partial u}{\partial t} + ((u - w) \cdot \nabla)u\right) = f - \nabla p + \mu \Delta u, \quad (1)$$

where u represents the velocity, w the reference velocity, t the time, f is a volume force, p the pressure and $\rho$ and $\mu$ the fluid density and viscosity, respectively. Obtaining a pressure distribution from its gradient given in Equation (1) is not straightforward. Most approaches identify spatial integration paths which are often significantly sensitive when applied to noisy input data. In order to include smoothing options and to avoid boundary condition sensitivities, the present invention starts with a higher-order pressure derivative which yields the PPE problem as the basis of the approach of the present invention. Rearranging Equation (1) for $\nabla p$ yields:

$$\nabla p = b, \quad (2)$$

where the right-hand side vector b is a function of given velocity data and depends on the constitutive properties of blood:

$$b = f + \mu \Delta u - \rho\left(\frac{\partial u}{\partial t} + ((u - w) \cdot \nabla)u\right). \quad (3)$$

The PPE is now defined as the divergence of Equation (2) and gives a higher order derivative of the pressure field p:

$$\Delta p = \nabla \cdot b. \quad (4)$$

Numerical Discretisation

In order to solve for cardiovascular pressure fields, the method of the present invention utilises a finite element based approach to the field of cardiovascular pressure estimation, driven by volume sources rather than surface fluxes. This has the advantage that not only the use of gradient boundary conditions is avoided but it also allows a reduction of the computational domain at a later stage.

A weak formulation is obtained by multiplying Equation (4) with the finite element test function q and subsequently integrating over the computational domain $\Omega$:

$$\int_\Omega (\nabla \cdot \nabla p) q d\Omega = \int_\Omega (\nabla \cdot b) q d\Omega, \forall q \in H^1(\Omega) \quad (5)$$

In the method of the present invention, the pressure estimation approach is based on applying integration by parts to both the left-hand and right-hand side of Equation (5), which yields the surface integral:

$$\int_\Gamma (\nabla p - b) \cdot n q d\Omega = 0,$$

leaving only the volume integrals $$\int_\Omega \nabla p \cdot \nabla q d\Omega = \int_\Omega b \cdot \nabla q d\Omega. \quad (6)$$

Following a standard Galerkin finite element discretisation, the matrix system $K_{mn}p_n = s_m$ for Equation (6) for m, n=1, . . . , N with the number of degrees of freedom (DOF) N, is obtained, and therefore, $$K_{mn} = \int_\Omega \nabla \varphi_n \cdot \nabla \varphi_m d\Omega = \int_\Omega \frac{\partial \varphi_n}{\partial x_k} \cdot \frac{\partial \varphi_m}{\partial x_k} d\Omega. \quad (7)$$

The right-hand side source is discretised as:

$$s_m = \int_\Omega b \cdot \nabla \varphi_m d\Omega = \int_\Omega b_k \cdot \frac{\partial \varphi_m}{\partial x_k} d\Omega, \quad (8)$$

with $$b_k = -\rho\underbrace{\left(\frac{\partial u_k}{\partial t} + (u_i - w_i)\frac{\partial u_k}{\partial x_i}\right)}_{acceleration\,terms} + \mu\underbrace{\frac{\partial^2 u_k}{\partial x_i \partial x_i}}_{viscous\,terms}. \quad (9)$$

The scalar function $\varphi_m$ represents the finite element test functions, $\varphi_n$ the basis functions for the resulting pressure field with m, n=1, N. The vector x contains global coordinates in D-dimensional space and i, k=1, . . . , D. It should be noted that Equation 9 accounts for both viscous and inertia terms. It can therefore be applied to the whole range of laminar, low- and high-Reynolds number flows.

In order to capture the second derivative terms correctly, a tri-cubic Lagrangian or hermite basis function is suited best for the finite-element implementation. The latter allows the improvement of real data quality by applying additional projection and data smoothing methods.

Embedded Pressure Poisson Approach

For the general purpose of cardiovascular pressure estimation, the embedded velocity fields are characterised by introducing the element-based labelling factor κ into Equation (6) which yields:

$$\tilde{K}_{mn} p_n = \kappa s_m \quad (10)$$

where $$\tilde{K}_{mn} = \int_\Omega \kappa (\nabla \varphi_m \cdot \nabla \varphi_n) d\Omega, \quad (11)$$

and $s_m$ is defined in Equation (8). Assuming a velocity screen procedure that results in a discretised domain Ω containing both the fluid domain of interest $\Omega_{int}$ and the surrounding area $\Omega_{ext}$, κ can now be used to perform the PPE computation without extra segmentation or mesh adaptation where κ=1 on $\Omega_{int}$ and κ=0 on $\Omega_{ext}$. Elements e are treated as boundary elements if one degree of freedom (DOF) of $\Omega^e$ is labeled as an outside voxel corresponding to $\Omega_{ext}$. Masking information may be treated as piecewise constant or, alternatively, evaluated and scaled with 0≤κ≤1. This avoids the propagation of $\Omega_{int}$-source signals to $\Omega_{ext}$ and any external influence from $\Omega_{ext}$ on $\Omega_{int}$.

Verification and Validation

In order to test the discretised PPE problem, the following verification process was performed, using a self-adjoint analytic solution of the form:

$$\Delta p = -\frac{12\pi^2}{L^2} p, \quad (12)$$

which represents a complex spatial pressure field $$p(x, y, z) = \sin\left(\frac{2\pi x}{L}\right) \sin\left(\frac{2\pi y}{L}\right) \sin\left(\frac{2\pi z}{L}\right) + p_0 \quad (13)$$

inside a regular cube with side length L=1 and reference pressure $p_0$=0. The numerical solution was applied under mesh refinement and for different orders of interpolation.

FIG. 1 illustrates an assessment of the convergence rate for the Poisson problem given in equation 12, as given by the slope for various orders of interpolation.

The results for mesh refinements by a factor of 2 are shown in FIG. 1, where r is the error measured as L2 norm, h represents element size and logarithmus dualis is defined as $ld(r)=\log_2(r)$. For linear, quadratic and cubic Lagrange interpolation order the corresponding graph exhibits the expected error convergence rate.

The present approach also gives accurate results when embedding given flow fields in a data acquisition space. Two different examples can be seen in FIG. 2 and FIG. 3 where $\Omega_{ext}$ (darkest) represents parts of Ω that do not contain any flow information, and $\Omega_{int}$ (lighter shades) represents the embedded field.

Figure 2:
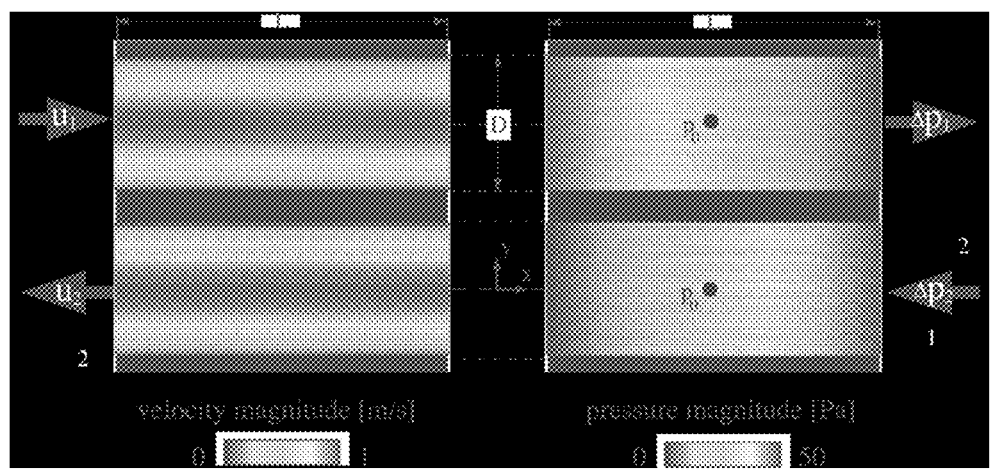
FIG. 2 depicts illustrates the flow in two aligned channels; D/L=0.4, $\mu$=1 Pa·s, $u_{max}$=1 m/s, $p_0$=25 Pa.

FIG. 2 illustrates the flow in two aligned channels; D/L=0.4, μ=1 Pa·s, $u_{max}$=1 m/s, $p_0$=25 Pa.

The left-hand side of FIG. 2 shows the velocity magnitude fields in $\Omega_{int}$ of two fully developed channel flows surrounded by $\Omega_{ext}$. Arrows indicate the respective flow direction resulting in one positive and one negative pressure gradient. The analytic values for velocity and pressure distribution are given by the following formulas:

$$u(y) = (D^2 - 4y^2)\frac{u_{max}}{D^2}, \; p(x) = p_0 - 8\mu x \frac{u_{max}}{D^2}, \quad (14)$$

respectively, where $u_{max}$ is the maximum velocity inside a channel with width D, flow direction x, centre line y=0 and reference pressure $p_0$. Due to the elimination of DOFs outside the fluid domain, the two respective pipe flows ($u_1$=u(y)=−$u_2$; $p_1$=p(x)=−$p_2$) are completely separated and isolated from each other.

Figure 3:
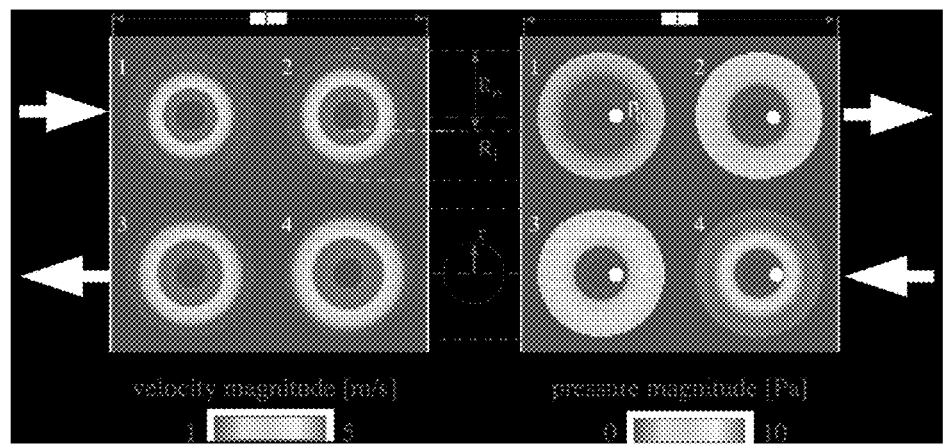
FIG. 3 depicts four pairs of rotating cylinders; $R_o/L$=0.2, $R_i/L$=0.05, $p_0$=0 Pa.

Whereas FIG. 2 represents a friction-driven test case, FIG. 3 shows the results of a third, inertia-driven test problem where velocity magnitude fields are generated by four pairs of cylinders (inner radius $R_i$, outer radius $R_o$) rotating at different speeds (inner velocity $\omega_i$, outer velocity $\omega_o$). The analytic values for velocity and pressure distribution are given by the following formula $$u(r) = \frac{C}{r}, \; p(r) = p_0 - \frac{C^2}{2r^2}, \quad (15)$$

with $R = R_i < r < R_o$ and $C = (9 + c/10)R^2 \cdot \frac{1}{s}$.

The left-hand side of FIG. 3 shows this linearly increasing velocity magnitude from case c=1 to case c=4; the right-hand side shows the expected increase of pressure on the outer wall of the cylinder system due to the increasing centrifugal forces. The calculated pressure level for all four cases is in very good agreement with the analytical values given by Equation (15). As in the previous example, all four velocity fields are mathematically isolated as needed for the following cardiovascular application.

The parameters for FIG. 2 and FIG. 3 have been chosen in a way that results in representative pressure fields. A different set of parameters would not result in a less accurate solution but in a less optimized graphical outcome. Therefore, parameters and R have been chosen in a way that the vertical geometric extension of each flow domain is 40% of the overall domain. With L=1, this means D=0.4 and R=0.2 in FIG. 2 and FIG. 3, respectively. Initial and constitutive parameters have been set to 1 (mu and $u_m$ax in FIG. 2), reference pressures to mid range ($p_0$=25 in FIG. 2 and $p_0$=0 in FIG. 3) to allow for a pressure scale starting from p=0.

As far as finite-element order and discretisation density is concerned, the convergence test example in FIG. 1 shows the expected decreasing error with an increasing number of elements. The test example in FIG. 2 can now be treated as separated fluid domains which has not been possible for conventional methods. For the first time, the resulting pressure distribution is entirely independent from the distance of the respective fluid domains. This advantage of the method of the present invention, becomes even more important when treating the second example in FIG. 3 where the pressure only depends on viscous resistance. This contribution has not been included in prior art methods. Without complete fluid domain separation, an independent linear pressure distribution in flow direction would show high sensitivity to the fluid domain distance.

Modelling and Application

Figure 4:
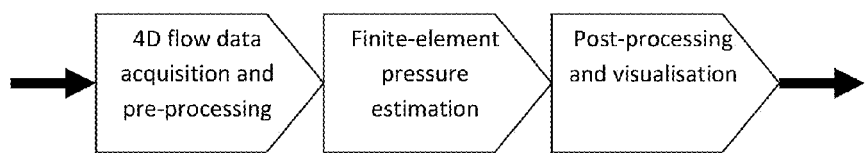
FIG. 4 is an evaluation workflow from 4D flow data over pressure estimation to visualisation of results.

The data processing approach described above is applied in order to estimate the velocity-based pressure field for a dataset of a healthy human subject. FIG. 4 explains the following workflow from data acquisition to pressure evaluation. Firstly, 4D flow data is acquired and a pre-processing step carried out. Then the finite-element pressure is estimated, followed by a post-processing and visualisation step. The following description provides full details of the steps outlined.

Data Acquisition and Processing

The velocity input for the method of the present method is provided by phase-contrast MR imaging, a technique that allows blood flow velocity to be measured and post-processed non-invasively. Measurements were performed on a 3T system (Magnetom Trio, Siemens AG, Erlangen, Germany) with a standard 8-channel phased-array coil. 4D flow data with three-directional velocity encoding and covering the whole heart fluid domain were acquired using a navigator respiration controlled and ECG-gated rf-spoiled gradient echo sequence (spatial resolution: 2.95×2.50×2.90 mm$^3$, temporal resolution: 38.4 ms, velocity encoding: 150 cm/s, time frames per cardiac cycle: 17).

Initial raw data normally contains magnitude and three-dimensional phase information for each voxel of the initial imaging space. Voxel-based phase shifts can be directly transformed into velocity vectors which marks the starting point for the method of the present cardiovascular pressure estimation. Data-processing was established to further enhance quality (e.g. eddy-current elimination, velocity aliasing or noise filtering) and to allow for fluid domain representation (i.e. MR segmentation and flow field masking). Noise masking can be performed by thresholding of the signal deviation of the magnitude data in order to exclude regions with low signal intensity. Further noise reduction and separation of static tissue and vessels is achieved by comparing the standard deviation of the velocity-time course for each pixel in the flow data set. MR segmentation output was used to mask geometric entities based on an averaged fluid domain representation.

The following procedures are typically applied before the 4D flow data enters the pressure estimation workflow: Anti aliasing, Noise masking, Eddy current reduction. Based on a "speed sum squares" iso-surface representation over all time-steps T $$\sigma = \sum_{j=1}^{T} \sum_{i=1}^{3} u_i^2(t_j) = \text{const.,} \quad (16)$$

an averaged segmentation of the cardiovascular geometry may be created. Since this iso-value represents the basis for fluid domain masking ($\Omega_{int}/\Omega_{ext}$), careful distinction of adjacent cavities or vessels is taken into account.

Pressure Estimation Workflow

In order to allow a smooth and straightforward representation of the cardiovascular geometry of interest, the present method follows the mean fluid domain approach. This approach is suitable for use in 4D flow analysis based on MR segmentation information.

Geometrical Representation

Figures 5A, 5B:
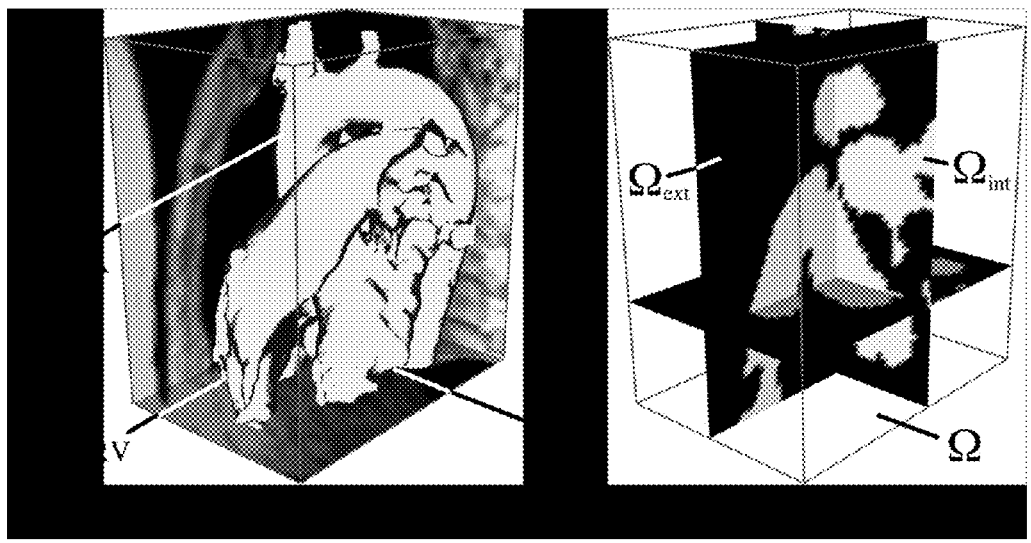
FIG. 5a depicts the "Speed-sum-square" segmentation inside imaging space a FIG. 5b provides mean fluid domain needed for $\Omega_{ext}/\Omega_{int}$ masking.

The left-hand side of FIG. 5 shows an isosurface (the lighter portions) of $\sigma$, defined in Equation (16), clearly indicating the left and right ventricle, the aorta and adjacent large vessels. Valid velocity information is available in the entire imaging space $\Omega$ (square box) following an Eulerian description approach. However, here, the focus is on the internal volume $\Omega_{int}$—with $\sigma$=0.2 m$^2$/s$^2$ set as lower bound—assuming $\Omega_{int}$ is a sub-domain of the true fluid domain over the whole cardiac cycle. This value has been chosen according to and can be estimated by assuming a mean aortic velocity between 0 and 1 present over 50% of the cardiac cycle. This value guarantees a separated representation of the aortic arch and must be optimized for the respective case under consideration.

Thresholds are set such that they allow for the best mean representation of the cardiovascular velocity field. Following this mean geometrical representation, the right-hand side of FIG. 5 now visualises the fluid domain masking and the subsequent separation of the whole imaging domain $\Omega$ into $\Omega_{int}$ and $\Omega_{ext}$. This information will be used in a similar way as for the cases in FIG. 2 and FIG. 3; they are also the basis for the numerical approach and its parameter settings for $\kappa$ in Equation (10).

Pressure Field Estimation

Figure 6:
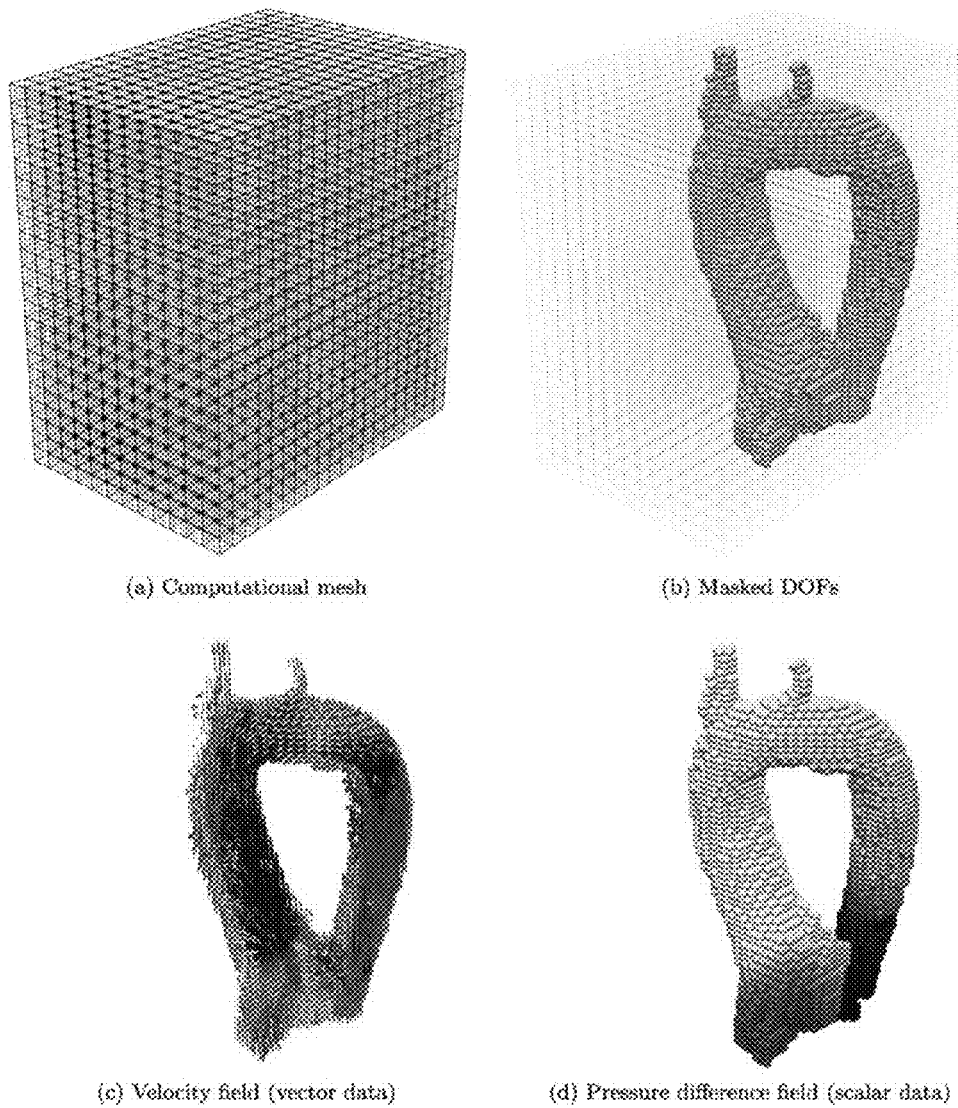
FIG. 6 illustrates the data processing from imaging space to pressure evaluation.

FIG. 6 shows the discretised imaging domain $\Omega$. However, following the masking efforts shown in FIG. 5, the masked DOFs can be used to distinguish between $\Omega_{int}$ and $\Omega_{ext}$. Whereas nodes which belong to $\Omega_{int}$ carry velocity information, all nodes of $\Omega_{ext}$ get eliminated from the initial computational domain, effectively decreasing the system size and, hence, increasing computational efficiency.

Visualisation and Post-Processing

Velocity Field and Estimated Relative Pressure

Figure 7A:
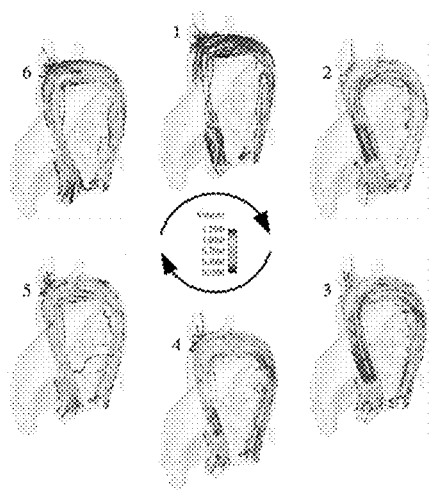
FIG. 7a illustrates the input velocity field projected on streamlines.
Figure 7B:
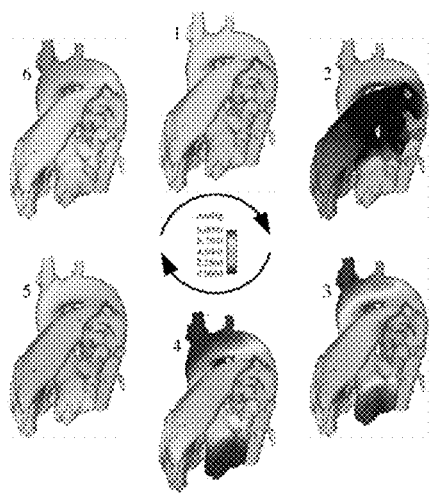
FIG. 7b illustrates the estimated pressure projected on fluid domain boundary.

The left-hand side of FIG. 7 shows 6 different snapshots at different points in time during systole chosen for best visualisation results. Starting with almost steady-state conditions (snapshot 1), one can clearly identify the increasing blood velocity magnitude in early systole (snapshots 2 and 3) and the blood momentum transported further downstream the aorta (snapshots 4 and 5) until the blood velocity magnitude decreases to a minimum (snapshot 6). The right-hand side shows the corresponding relative pressure fields directly computed from the respective time-frames.

Since there is almost no blood flow present at the very beginning of systole (snapshot 1) no differences of relative pressure can be identified. However, as soon as the early systole begins, a pressure drop over the aortic valve plane can be seen (snapshot 2) followed by an increase of both the magnitude and differential values of the relative pressure field (snapshot 3). After the main blood flow has passed the aortic arch, the highest relative pressure value develops due to the centrifugal forces (snapshot 4). Finally, the relative pressure field returns to its initial state (snapshot 5 and 6). The reference point for the relative pressure field has been located at the end of the descending aorta. Pressure values are measured relative to the pressure at this reference point.

Spatial and Temporal Correlation

Analysing the spatial and temporal correlation of velocity and pressure, it must be noted that the results presented are currently gained from one volunteer only. In order to clarify the velocity/pressure interdependence, in FIG. 8, the velocity and pressure magnitudes for three different time-frames during the systolic phase are plotted. Two different cutting planes (one through the aorta and one through the ventricle) are used to project and visualise both velocity magnitude and pressure. Relative to the reference point at the end of the descending aorta, one can clearly identify a pressure drop during early systole followed by the highest pressure in the aortic arch as a consequence of the stagnation pressure and the change of direction of the blood column.

Figure 8:
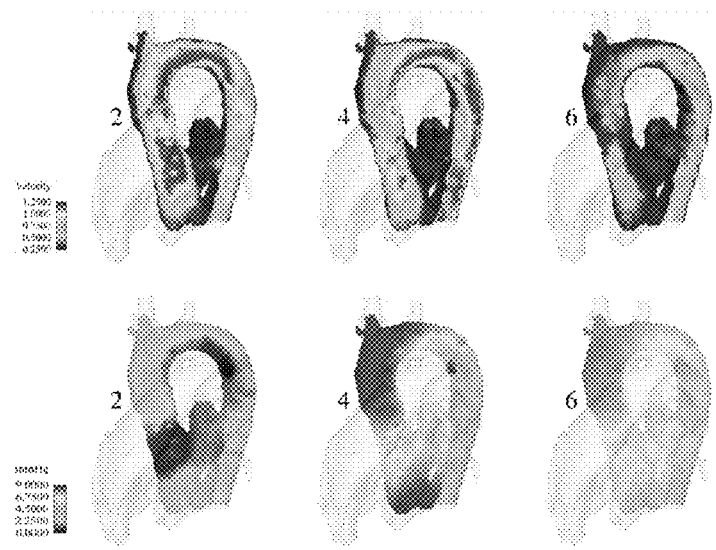
FIG. 8 illustrates the velocity (top three diagrams) and pressure magnitudes (bottom three diagrams) on cutting planes.
Figure 9:
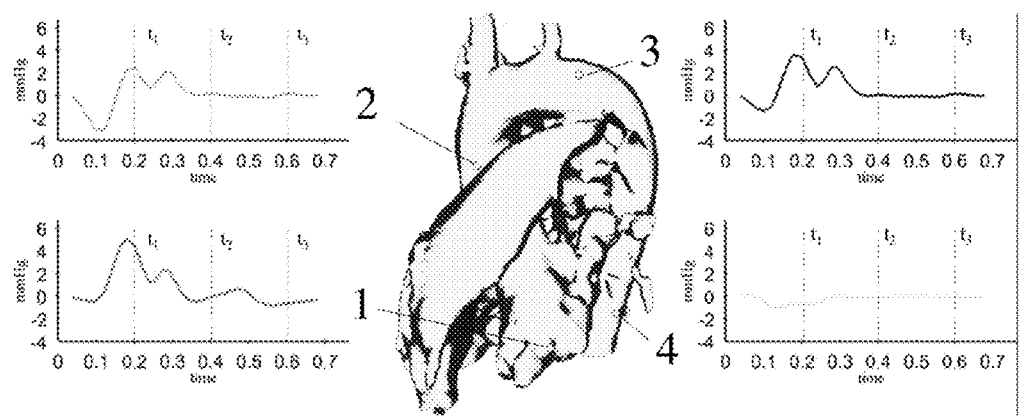
FIG. 9 illustrates the local relative pressure dynamics.
Figure 10:
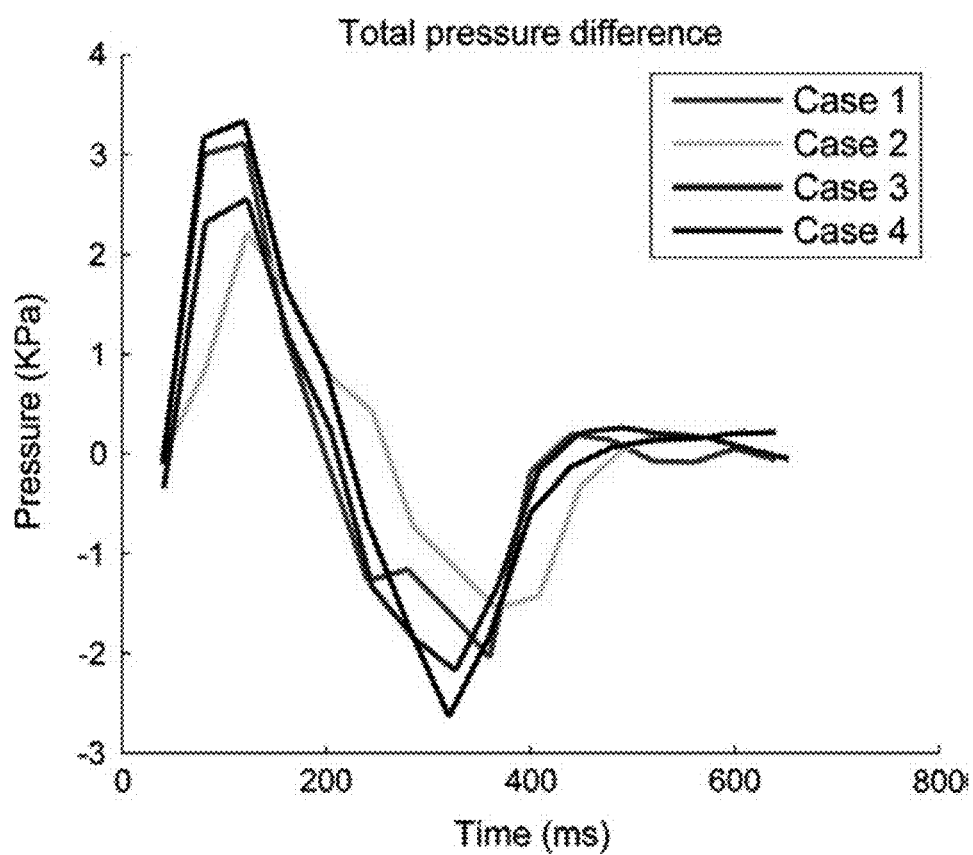
FIG. 10 is a graph illustrating the temporal transients of the pressure difference between the left ventricle and the end of the descending aorta in the four healthy volunteers.

Whereas FIG. 8 gives a first indication of the spatial relation between velocity and pressure, FIG. 9 allows a temporal analysis of the cardiac cycle. Point 1 is placed inside the left ventricle, followed downstream by points 2 and 3 until the end of the descending aorta is reached at point 4; close to the pressure reference point. The early systole causes positive and negative relative pressure changes at points 1 and 2, respectively, before the pressure level returns to its force-free state. The effect of the directional change due to the aortic arch causes an earlier pressure increase accompanied by a higher magnitude. Control point 4 shows no significant pressure change, being located at the end of the descending aorta.

In the method of the present invention, a Pressure-Poisson-based estimation process within a multi-physics finite element method is used. Pressure field values are directly calculated without the requirement of iterative processes and boundary conditions. Measured 4D flow data have been used to identify volume source distributions which represent the only driving force of an underlying pressure estimation process; the determination of sensitive boundary conditions is thus avoided. The method of the present invention, thus, accounts for pressure changes due to both acceleration and viscous resistance and is thus, advantageously, valid for both low- and high-Reynolds number laminar flows. The method of the present invention provides a platform for a wide range of applications both in clinically relevant diagnosis and in computational cardiac modelling.

Volume Source Field Projection

This method of the present invention follows a treatment of the numerical boundary conditions which has a significant influence on the overall pressure estimation work-flow. On the one hand, the so-called Neumann boundary conditions are based on gradients of the underlying velocity field and show a high sensitivity when derived from noisy data. On the other hand, the Neumann conditions need to be applied properly to the actual fluid domain boundary which normally lies inside the imaging domain, e.g. when considering a normal 4D flow study. The significance of the present approach has the advantage that it avoids the need to determine Neumann conditions. It can therefore be applied to a segmented fluid domain but also directly to the initial imaging space without any difference to the pressure estimation result.

Therefore, the present invention has the advantages that it allows additional data enhancement (divergence-free or $C^1$ conditions) and, the source field formulation allows the complete elimination of the outside domain. The isolation of the volume source field is also directly related to a speed-up in computational time. Since only the internal flow region contributes to the numerical problem size, there is a direct time advantage given by the ratio of internal to overall imaging space. In addition, the present method is directly able to determine the pressure distribution in one iteration only, i.e. almost real-time.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

The invention claimed is:

1. A non-iterative method for determining relative pressure within soft tissue of a subject, comprising:
   a) positioning the subject in association with a scanner;
   b) selecting a region of interest in the subject comprising soft tissue and blood flow;
   c) collecting flow data using the scanner over an imaging space within the region of interest, wherein the flow data comprises viscous, temporal, and spatial pressure components that contribute to pressure values;
   d) transforming the flow data into velocity data comprising one or more velocity vectors;
   e) determining tissue geometry and flow measurement points within the imaging space, wherein the imaging space comprises an internal imaging space and an external imaging space, and separating the imaging space into fluid and solid domains;
   f) generating a computational mesh based on the velocity data collected at the flow measurement points within the fluid domains;
   g) masking out the external imaging space;
   h) reducing the computational mesh based on the region of interest;
   i) determining relative pressure data within the internal imaging space using the reduced computational mesh, wherein determining the relative pressure data comprises Gaussian integration and finite-element discretization;
   j) post-processing the relative pressure data;
   k) visualizing the post-processed relative pressure data; and
   l) visualizing pressure components within the relative pressure data, wherein the pressure components comprise viscous, temporal, and spatial components that contribute to the relative pressure data.

2. The method of claim 1, wherein the scanner is a magnetic resonance or an ultrasound scanner.

3. The method of claim 1, wherein the flow data is 4D flow data.

4. The method of claim 1, wherein the flow data is time-resolved velocity data.

5. The method of claim 1, wherein the flow data comprises information on temporal acceleration, spatial acceleration, and viscous dissipation.

6. The method of claim 1, further comprising flow data pre-processing after collecting the flow data.

7. The method of claim 6, where the pre-processing comprises one or more of eddy-current elimination, velocity aliasing, noise filing, MR segmentation, flow field masking, cardiovascular geometry determination, individually or any combination thereof.

8. The method of claim 1, further comprising gating the collecting of the flow data to one or more cardiac cycles, one or more respiratory cycles, or both.

9. The method of claim 8, wherein determining tissue geometry within the imaging space is performed by assuming a mean aortic velocity between 0 and 1 present over 50% of the cardiac cycle.

10. A non-iterative method for determining relative cardiovascular pressure, comprising:
   a) positioning a subject in association with a scanner;
   b) selecting a region of interest in the subject comprising the heart;
   c) collecting flow data using the scanner across an imaging space within the region of interest, wherein the flow data comprises velocity data with phase shifts and viscous, temporal, and spatial pressure components that contribute to cardiac pressure values, and separating the imaging space into fluid and solid domains;
   d) transforming the phase shifts in the flow data into velocity data comprising one or more velocity vectors;
   e) pre-processing the velocity data;
   f) generating a computational mesh based on velocity data at flow measurement points within the fluid domains of the imaging space;
   g) determining cardiovascular geometry based on the computational mesh, the velocity data, and a reference and determining an image space comprising an internal cardiac image space and an external cardiac image space;

h) masking the image space to exclude the external cardiac image space;

i) reducing the computational mesh based on the masked image space and region of interest;

j) generating relative finite-element pressure data within the internal cardiac image space from the reduced computational mesh;

k) post-processing the relative finite-element pressure data; l) visualizing the relative finite-element pressure data; and m) visualizing the viscous, temporal, and spatial pressure components that contribute to cardiac pressure values for determining the relative cardiovascular pressure.

11. The method of claim 10, wherein the velocity vectors comprise encoded information on temporal acceleration, spatial acceleration, and viscous dissipation.

12. The method of claim 10, wherein generating finite-element pressure data further comprises:

k) separating the pressure data into the components of transient and convective momentum, viscous resistance and volume forces;

l) transforming the separated pressure data to include smoothing options and avoid boundary conditions;

m) determining a weak formulation of the pressure fields by multiplying the transformed separated pressure data by a finite element test function and integrating across computational domain $\Omega$ using Gaussian integration;

n) performing Galerkin finite element discretization on the weak formulation of the pressure fields; and o) determining the pressure fields by introducing element-based labelling factor $\kappa$ to the volume integrals derived from the weak formulation of the pressure fields, using $\kappa$ to determine relative pressure from known flow fields, and using $\kappa$ values for masking $\Omega$ into $\Omega_{int}$ and $\Omega_{ext}$, wherein $\kappa=1$ on $\Omega_{int}$ and $\kappa=0$ on $\Omega_{ext}$, and masking is scaled with $0 \leq \kappa \leq 1$.

13. The method of claim 10, wherein the scanner is a magnetic resonance or ultrasound scanner.

14. The method of claim 10, wherein the flow data is 4D flow data.

15. The method of claim 10, wherein the flow data is time-resolved velocity data.

16. The method of claim 10, wherein the flow data comprises information on temporal acceleration, spatial acceleration, and viscous dissipation.

17. The method of claim 10, where the pre-processing comprises one or more of eddy-current elimination, velocity aliasing, noise filing, MR segmentation, or flow field masking, cardiovascular geometry determination, individually or any combination thereof.

18. The method of claim 10, further comprising gating the collecting of the flow data to one or more cardiac cycles, one or more respiratory cycles, or both.

19. The method of claim 17, wherein cardiovascular geometry determination is performed by assuming a mean aortic velocity between 0 and 1 present over 50% of the cardiac cycle.

20. A non-iterative method for determining relative cardiovascular pressure, comprising:

a) positioning a subject in association with a scanner;

b) selecting an area of interest in the subject;

c) collecting 4D flow data at measurement points in the area of interest in the subject with a scanner, wherein the 4D flow data comprises viscous, spatial, and temporal pressure components that contribute to relative cardiovascular pressure;

d) mapping cardiovascular geometry and separating fluid and solid domains in the area of interest;

e) generating a computational mesh from the 4D flow data collected at measurement points within the fluid domain;

f) determining relative cardiovascular pressure from the computational mesh; and g) visualizing relative pressure and the pressure components that contribute to relative cardiovascular pressure.

21. The method of claim 20, wherein the scanner is a magnetic resonance or ultrasound scanner.

22. The method of claim 20, wherein the 4D flow data is time-resolved velocity data.

23. The method of claim 20, wherein the 4D flow data comprises information on temporal acceleration, spatial acceleration, and viscous dissipation.

24. The method of claim 20, further comprising gating the collecting of the 4D flow data to one or more cardiac cycles, one or more respiratory cycles, or both.

* * * * *